(12) United States Patent
Chang

(10) Patent No.: US 9,943,157 B1
(45) Date of Patent: Apr. 17, 2018

(54) SWAB APPLICATOR WITH DISPENSING PASSAGE

(71) Applicant: Unicep Packaging, LLC, Sandpoint, ID (US)

(72) Inventor: Lorrin Edward Chang, Sandpoint, ID (US)

(73) Assignee: Unicep Packaging, LLC, Sandpoint, ID (US)

( * ) Notice: Subject to any disclaimer, the term of this patent is extended or adjusted under 35 U.S.C. 154(b) by 0 days.

(21) Appl. No.: 15/353,563

(22) Filed: Nov. 16, 2016

(51) Int. Cl.
*B43K 5/14* (2006.01)
*A45D 34/04* (2006.01)
*A61F 13/40* (2006.01)

(52) U.S. Cl.
CPC ......... *A45D 34/042* (2013.01); *A61M 35/006* (2013.01)

(58) Field of Classification Search
CPC .................................................. A61M 35/006

USPC .................................. 401/133, 130; 604/2, 3
See application file for complete search history.

(56) References Cited

U.S. PATENT DOCUMENTS

| | | | | |
|---|---|---|---|---|
| 5,152,742 A | * | 10/1992 | Simpson | A45D 34/042 401/132 |
| 5,830,186 A | * | 11/1998 | Gonzales | A61M 31/00 604/131 |
| 2003/0181840 A1 | * | 9/2003 | Tsaur | A61F 13/38 604/1 |
| 2011/0295211 A1 | * | 12/2011 | Yeager | A61M 35/006 604/187 |
| 2016/0302776 A1 | * | 10/2016 | Adolphson | A61B 10/0096 |

* cited by examiner

*Primary Examiner* — Jennifer C Chiang
(74) *Attorney, Agent, or Firm* — Lee & Hayes, PLLC

(57) ABSTRACT

In some implementations, an applicator includes a container and an insert disposed in the container. The insert may include a flange extending radially outwardly from an elongate post, and a porous tip covering the flange. A passageway is provided to convey, via material comprising the porous tip, a substance contained in the container to an external surface of the porous tip for application.

20 Claims, 4 Drawing Sheets

SWAB APPLICATOR WITH DISPENSING PASSAGE

BACKGROUND

Many compositions, e.g., liquids, gels, and the like, are provided in bulk, for subsequent use or application. For instance, cosmetics, ointments, oral care products, and adhesives are commonly provided in a container and applied using a separate applicator such as a swab or brush. Alternatively, some containers have integrated applicators, which may include brushes, nozzles, or swabs built into the packaging. Some such containers are single-use, whereas others are re-sealable and capable of repeated use, i.e., until the bulk is fully consumed.

Conventional containers with separate applicators may be unsatisfactory because one of the container and the applicator is frequently misplaced. Moreover, commercially available containers with integrated applicators are generally difficult to use.

SUMMARY

This application describes applicators that include a reservoir for containing a substance and an integrated porous tip, such as a swab, for applying the substance. The applicator includes one or more dispensing passageways through which the substance travels from the reservoir to the applicator for application. Applicators according to this disclosure may be single-use or multiple use, and may provide a simple package for ready application of a flowable substance.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
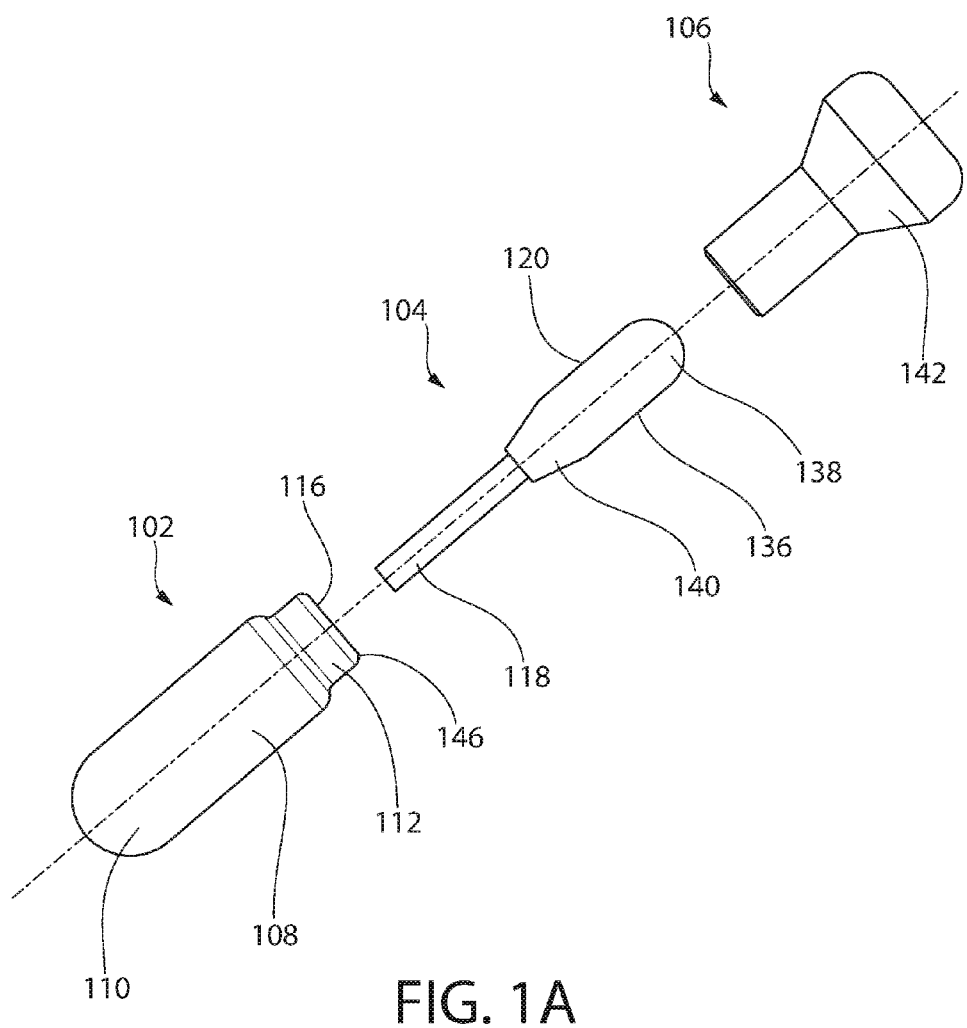
FIG. 1A is an exploded perspective view of an applicator according to embodiments of this disclosure.

This disclosure describes improved applicators, and methods of making applicators. In some implementations of this disclosure, an applicator may include a container defining a reservoir for holding a substance and a swab for applying the substance. The swab may be retained in an opening in the container, such that a portion of the swab is exposed to the reservoir and a second portion of the swab extends from the container. One or more passageways may extend through a portion of the swab, through which bulk contained in the reservoir enters a tip of the swab. The container may be deformable, and deformation of the container may cause the reservoir to compress, thereby forcing substance in the reservoir to an outer surface of the tip of the swab, via the passageway(s).

In some implementations, the container may include a neck defining an opening, and the swab may be retained in the neck. For example, an outer surface of the swab may form an interference fit with the inner surface of the neck of the container, thereby retaining the swab in the container. In implementations, the container may also include a removable cover. Before removal, the cover covers the swab, such that substance in the container does not inadvertently leak or otherwise leave the applicator. The cover may be retained on a base of the container via a frangible connection. In this example, the cover may be removed by application of a shear force sufficient to break the In some implementations, a swab may include a post extending between a proximal end and a distal end. A flange may be disposed on the post, extending radially from an outer surface of the post, between the proximal end and the distal end. The passageways may extend from a first side of the flange, closer the proximal end, and a second side of the flange, closer the distal end, such that the substance to be applied passes from the first side of the flange to the second side of the flange via the passageways. In some implementations, the passageways may comprise one or more through holes or openings formed through the flange. The passageways may also include one or more grooves formed on an outer surface of the flange.

In implementations of this disclosure, a porous tip may be fixed on the distal end of the post. For instance, the porous tip may be an open-cell foam through which liquids or other substance can flow. In some examples, the porous tip covers the passageways, such that the substance contained in the applicator flows through both the passageways and the porous tip before being applied via an outer surface of the porous tip. The porous tip may have a bulbous shape, much like a conventional cotton swab, or may have alternative shapes, e.g., for specific application uses.

For discussion purposes, some example implementations of applicators are described in connection with applying certain types of bulk substance. However, the implementations herein are not limited to the particular examples provided, and may be extended to other types of bulk, as will be apparent to those of skill in the art in light of the disclosure. The specific features and acts are disclosed as example forms of implementing the claims.

Figure 1B:
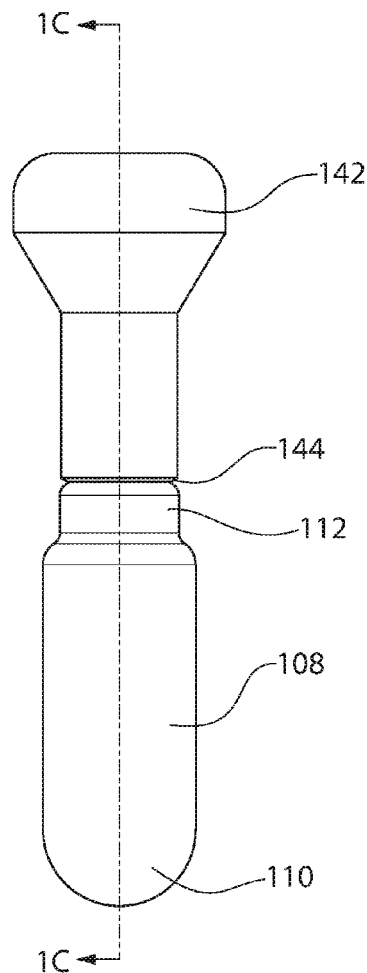
FIG. 1B is a plan view of the example applicator shown in FIG. 1A, according to embodiments of this disclosure.
Figure 1C:
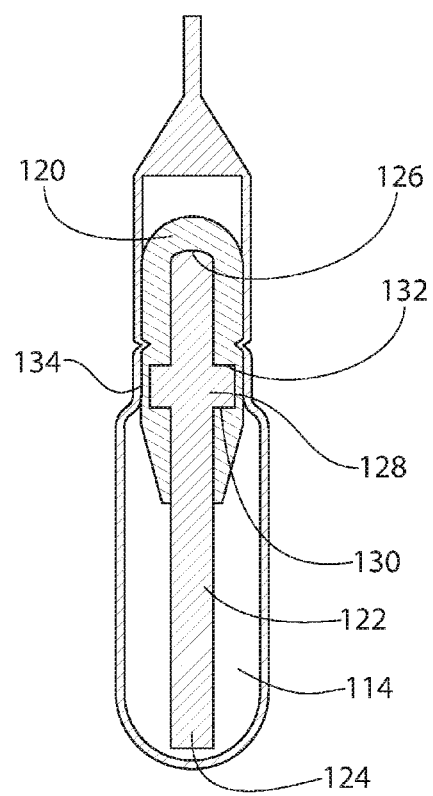
FIG. 1C is a cross-sectional view of the applicator of FIG. 1, taken along section line A-A in FIG. 1B.

FIGS. 1A-1C illustrate an applicator 100 according to embodiments of this disclosure. More specifically, and as illustrated in the exploded view of FIG. 1A, the applicator 100 generally includes a container 102, an insert 104 adapted to be retained in the container 102, and a removable cap 106.

The container 102 according to the illustrated embodiment is generally cylindrical and includes a sidewall 108 extending between a closed base 110 and a neck 112. The sidewall 108, base 110, and the neck 112 generally define a volume or reservoir 114 (shown in FIG. 1C), and the neck 112 defines an opening 116 that accesses the reservoir 114.

Although the illustrated container 102 is generally cylindrical, other shapes may be used. For example, the sidewall 108 may include one or more planar surfaces and/or may be tapered between the base 110 and the neck 112. Moreover, while the closed base 110 is illustrated as being generally domed, in alternative embodiments, the closed base 110 may be generally planar or include a planar surface. For instance, the closed base 110 may include a planar surface generally perpendicular to a longitudinal axis of the container 102. In this manner, the container 102 (and therefore the applicator 100) may be stood on the base 110, i.e., on a horizontal surface. Other modifications will also be appreciated. Functionally, it is generally only required that the container 102 define the reservoir 114 that can hold a substance to be applied by the applicator 100.

The container 102 may be deformable such that a user can readily decrease the volume of the reservoir 114, i.e., to force contents of the container 102 toward and, in some instances, through the opening 116. For instance, the sidewall 108 and/or the base 110 may be flexible such that a user can displace them toward a middle of the reservoir 114, e.g., by squeezing. In other embodiments, the container 102 may be relatively rigid, with contents contained in the reservoir 114 being expelled from the reservoir 114 through the opening 116 when the container 102 is tipped or tilted sufficiently to allow gravity to move the contents to and potentially through the opening 116.

In some implementations, the container 102 may be manufactured via a blow-fill-seal process. Other manufacturing techniques are also contemplated, for example, a blow-molding process, an injection molding process or any other manufacturing process suitable for forming the container. Depending on the product to be contained in the container for application and the manufacturing process, the container may comprise a polymer, such as polyethylene, ethyl vinyl alcohol copolymer or any other suitable polymer, mixture or the like that is suitable for forming the container. For example, low-density polyethylene (LDPE), high-density polyethylene (HDPE) or, polypropylene (PP) may be used to form the container.

The insert 104 generally includes a post 118 and a porous tip 120 disposed on a distal end of the insert 104. As illustrated in FIG. 1C, the post 118 generally comprises an elongate sidewall 122, extending along an axis between a proximal end 124 and a distal end 126. The sidewall 122 is illustrated as being substantially cylindrical, although additional shapes may be used. In the embodiment illustrated in FIGS. 1A-1C, the post 118 is solid, and also includes a flange 128 that extends radially outwardly (i.e., relative to the axis) from the sidewall 122. The flange generally includes a first side 130, closer the proximal end 124 of the post 118, and a second side 132 spaced from the first side, closer the distal end 126 of the post 118. The flange also include an outer surface 134 extending between the first side 130 and the second side 132.

In the illustrated embodiment, the first side 130 and the second side 132 are generally planar, and parallel to each other, separated by a thickness. In other embodiments, the first side 130 and the second side 132 may be angled relative to each other and one or both may be contoured and/or stepped. Functionality of the post 118 and the flange 128 will be described in more detail below, for example, with reference to FIGS. 2A and 2B.

In some implementations, the post 118 may be manufactured using an injection molding process. Other manufacturing techniques are also contemplated, for example, a machining process or any other manufacturing process suitable for forming the post 118. The post may be relatively rigid and is generally non-porous. For example, the post 118 may comprise a polymer, such as polypropylene. Other materials, including LDPE, HDPE, and non-polymeric materials may also be used to form the post 118.

As illustrated best in FIGS. 1A and 1C, the porous tip 120 is positioned on the post 118 to cover the flange 128 and the distal end 126 of the post 118. In the illustrated embodiment, the porous tip generally includes a central, cylindrical portion 136, a domed tip 138, and a tapered portion 140 that tapers from the cylindrical portion 136 to the post 118. In other embodiments, the porous tip may take any number of shapes and contours, e.g., depending upon functional, aesthetic, and/or other considerations.

The porous tip 120 generally comprises a porous material through which a flowable material, e.g., liquid, gel, or the like, may pass. More specifically, in operation, the substance contained in the reservoir is absorbed into the porous tip and expelled from the tip, e.g., at an outer surface of the domed tip 138, when the domed tip contacts a surface to which the substance is to be applied. Thus, the porous material comprising the porous tip 120 may be chosen for its compatibility with the substance contained in the reservoir, i.e., because it allows the substance to flow through the tip. For example, the porous tip may comprise open cell foam, natural or synthetic cellulose fibers, e.g., cotton or flock, or the like.

The porous tip may be fixed to the post using conventional manufacturing processes. For example, the tip may be adhered, welded, or otherwise mechanically fixed to the post. The process for disposing the tip on the post may depend upon the materials used for the post and/or the porous tip. Moreover, the substance to be applied by the applicator 100 may also factor into the type of connection used. For instance, some substances for application may not be compatible with adhesives, and could cause the adhesive to fail.

As illustrated in FIG. 1C, the insert 104 may be disposed in the container 102 such that a portion of the porous tip 120 extends from the container 102, through the opening 116. In this embodiment, the proximal end 124 of the post 118 is disposed near the base 110 of the container 102. As also illustrated, the insert 104 may be disposed such that the flange 128 is disposed in the neck 112 of the container 102, and the outer surface of the cylindrical portion 136 of the porous tip 120 contacts an inner surface of the neck 112. In some embodiments, the outer surface of the cylindrical portion 136 of the porous tip 120 forms an interference fit with the inner surface of the neck 112, to retain the insert 104 in the container 102. In this arrangement, there is some clearance between the outer surface 134 of the flange 128 and the inner surface of the neck 112, although that clearance is filled by the material comprising the porous tip 120.

As also illustrated in FIGS. 1A-1C, a distal end of the neck 112 may be turned in. More specifically, a flange or lip 146 may be provided at the distal end of the neck 112 that extends radially inwardly, toward the axis. By providing an effectively narrower opening, the lip 146 may increase the interference between the neck 112 and the porous tip 120. For instance, the lip 146 may pinch or otherwise compress the outer surface of the porous tip 120.

The cap 106 is generally disposed to cover the porous tip 120, e.g., so the substance does not inadvertently leave the applicator through the tip and/or so the tip 120 does not become contaminated. In some embodiments, the cap 106 is frangibly coupled to the container 102. The cap 106 may be any type of device that is configured to seal the cover the porous tip 120 (e.g., a tab, a knob, a seal, a lid, etc.) and is configured to be removed (e.g., break off, etc.) upon application of a predetermined force. When the cap 106 is removed, the porous tip is exposed, allowing a user to apply the contents of the reservoir via the porous tip. In FIGS. 1A and 1B, the cap 106 is illustrated as including a grip or tab 142. A user may grasp the tab and rotate (such as about arrow A in FIG. 1B) or bend the tab 142, and thus the cap 106, relative to the container 102. This relative movement may break a frangible connection 144, which may be a score mark or similar weakened area proximate an end of the neck 112. In some applications, the cap 106 may be molded as part of the container 102.

Modifications to the cap 106 also are contemplated. For example, the tab 142 may take any shape or form other than the illustrated shape. Moreover, the cap may be attached in different manners. For example, the cap may be threaded onto the container instead of attached at the frangible connection 144. For instance, threads may be formed on an exterior surface of the neck, and cooperating threads may be formed on an inner surface of the cap 102. Of course, such a cap would necessarily have a larger interior diameter than the outer diameter of the neck, unlike the cap 102 illustrated. A threaded cap may facilitate re-attachment of the cap 106 to the container 102, for example, to promote re-use of the applicator 100. In other examples, the applicator may be intended as a single-use, e.g., by including an amount of the substance to be applied that is sufficient for only a single use. In another modification, an external wrapping or tape may be provided to seal the cap 106 relative to the container 102.

In operation, a user removes the cap 106 from the container 102 to reveal the porous tip 120. The user then manipulates the container 102 to force the substance contained in the container 102 to contact the porous tip 120, e.g., at the tapered portion 140 and/or the cylindrical portion 136 of the porous tip 120. For example, the user may squeeze or otherwise deform the container 102 to reduce the volume of the reservoir and/or the user may tip the applicator 100. Upon contacting the porous tip 120, the material then propagates through the porous tip, i.e., between the flange 128 and the inner surface of the neck 112, to the portion of the tip disposed outside the container. When the tip contacts a surface, the substance is transferred from the tip to the surface. Thus, the clearance between the outer surface 134 of the flange 128 and the inner surface of the neck 112 serves as a passageway allowing the substance in the applicator to go from the portion of the tip 120 arranged proximate the first side 130 of the flange 128 to the portion of the tip 120 proximate the second side 132 of the flange 128. If the applicator 100 is intended to be reusable, the cap 106 may be placed back on the applicator 100 to cover the porous tip 120. Alternatively, the applicator 100 may be recycled or otherwise disposed of.

Figure 2A:
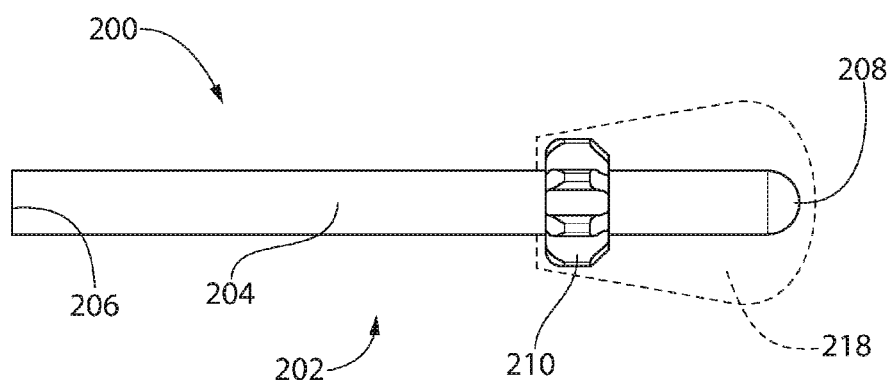
FIG. 2A is a side, plan view of a post comprising a portion of a swab for use in an applicator, such as the applicator shown in FIGS. 1A, 1B, and 1C, according to embodiments of this disclosure.
Figure 2B:
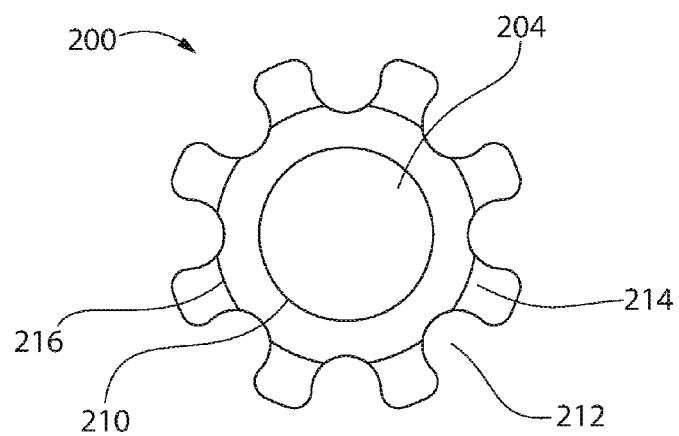
FIG. 2B is an end, plan view of the post illustrated in FIG. 2A.

As noted above, in the example configurations illustrated in FIGS. 1A-1C, a passageway may be provided at the clearance between the outer surface 134 of the flange 128 and the inner surface of the neck 112. Additional or alternative passageways may also be provided. For instance, FIGS. 2A and 2B are two views of an insert 200, which may be the insert 104 shown in FIGS. 1A-1C.

The insert 200 includes a post 202 having a generally elongate sidewall comprising a shaft 204 extending along an axis between a proximal end 206 and a distal end 208. The post 202 also includes a flange 210, similar to the flange 128. A plurality of axially-arranged grooves 212 are formed in an outside surface of the flange 210. As a result, a series of protrusions 214 extend radially outwardly from the shaft 204. When the insert 200 is disposed in the container 102, outer edges 216 of the protrusions 214 are arranged proximate an inner surface of the neck 112 and the grooves 212 form passageways for the fluid contained in the reservoir, in addition to any passageway formed at a clearance between the outer edges 216 and the inner surface of the neck 112.

As in the embodiments described above with reference to FIGS. 1A-1C, the insert 200 also includes a porous tip 218 (shown in dashed lines in FIG. 2A for clarity), like the porous tip 120. The porous tip 218 is disposed on the post 202 to cover the flange 210 and the distal end 208. The porous tip 218 has a slightly different shape than the tip 120, but generally functions in the same manner. The tip 218 could have other shapes and/or sizes.

The grooves 212 and the protrusions 214 may be sized and/or positioned in a number of ways, depending upon the application. For instance, larger grooves 212 can be formed to increase the size of the passageways and/or more passageways can be provided to increase an overall volume of all passageways combined. Conversely, smaller grooves can be used to decrease the size of the passageways and/or fewer grooves 212 can be provided to decrease the overall volume of all passageways combined. In aspects of this disclosure, the substance to be applied by the applicator may dictate the size and/or number of the passageways. For example, a more viscous liquid or gel may require larger and/or more grooves 212 (and/or a larger clearance between the flange 210 and the neck 112) whereas a less viscous liquid may need smaller and/or fewer grooves (or no grooves at all).

Figure 3:
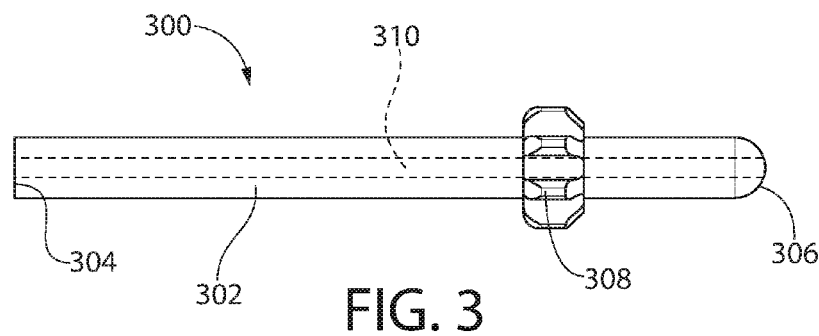
FIG. 3 is a plan view of a post for use in an applicator, such as the applicator shown in FIGS. 1A, 1B, and 1C, according to embodiments of this disclosure.
Figure 4:
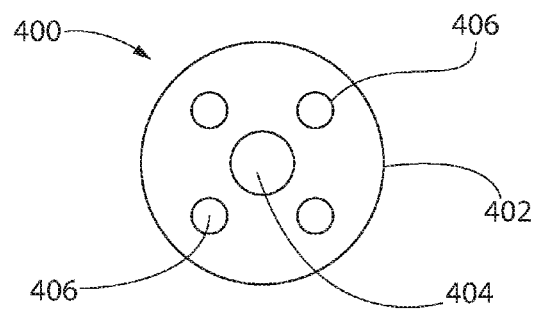
FIG. 4 is an end, plan view of a post comprising a portion of a swab for use in an applicator, such as the applicator shown in FIGS. 1A, 1B, and 1C, according to embodiments of this disclosure.
Figure 5:
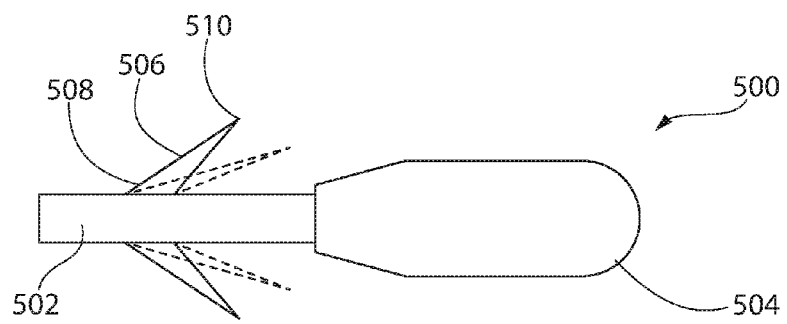
FIG. 5 is a plan view of an insert for use in an applicator, such as the applicator shown in FIGS. 1A, 1B, and 1C, according to embodiments of this disclosure.

FIGS. 3, 4, and 5 show other modifications that may be incorporated into applicators, such as the applicator 100 according to embodiments of this disclosure.

FIG. 3 is a plan view of a post 300, similar to the post 118 and the post 202 described above. The post 300 includes a shaft 302 extending along an axis between a proximal end 304 and a distal end 306. The post 300 also includes a flange 308 extending radially outwardly from the shaft 302. However, unlike the embodiments described above, the post 300 includes a passageway 310 extending through the shaft 302, generally along the axis. The passageway 310 may be provided in addition to or as an alternative to passageways provided between the outer surface of the flange 308 and an inner surface of the neck. For example, the post 300 may also include grooves in an exterior surface of the flange 308, like the grooves 212 shown in FIG. 2B.

FIG. 4 is an end view of a post 400 similar to posts described above. The post 400 generally includes a flange 402 extending radially outwardly from a shaft 404. A plurality of passageways 406 are also provided in the post 400, as through holes extending through the flange 402. The passageways may be in addition to or as an alternative to grooves, like grooves 212 and/or a passageway through the shaft 404, like the passageway 310. As with the grooves 212, the passageways 406 may be varied in size and/or number depending upon the application.

FIG. 5 illustrates an insert 500, which may be used in the same manner as the insert 104 or the insert 200 described above. For instance, the insert 500 includes a post 502 and a porous tip 504 disposed on the post 502. Unlike inserts described earlier, however, barbs 506 are provided on the post 502. As illustrated, the barbs 506 generally comprise elongate protrusions extending from post 502 at an angle relative to an axis of the post 502. More specifically, the barbs 506 extend from a base 508 proximate the post 502 to a distal end 510 spaced from the post 502, but closer to the porous tip 504 in the axial direction. The barbs 506 may be flexible such that the distal end 510 may be relatively closer to or farther away from the post 502. For example, the base 508 may serve as a living hinge or pivot about which the barbs 506 flex. In some embodiments, the barbs 506 may flex to the position shown in dashed lines in FIG. 5 to allow the insert 500 to be inserted into a container, such as the container 102. For example, as the insert 500 is pushed into the container, the barbs may contact the neck of the container and be forced into a flexed position. Once fully inserted into the container, the barbs 506 return to the non-flexed position, shown in solid lines in FIG. 5. In this position, any attempt to remove the insert 500 will cause the distal ends 510 of the barbs to be forced further outward, inhibiting passage of the barbs 506 through the neck. Accordingly, the insert 500 is retained in the container. The barbs 506 may be incorporated into any of the embodiments described above. Moreover, although two barbs are illustrated in FIG. 5, more or fewer barbs may be used.

According to embodiments of this disclosure, the applicator and each of the applicators constituent parts may be formed of a polymer, such as polyethylene, polypropylene, ethyl vinyl alcohol copolymer or any other suitable polymer, mixture or the like that is suitable for forming the applicator. The porous tip may be formed from any porous material, synthetic or naturally-occurring. In some examples, the porous tip is formed from open cell foam.

The applicator may be manufactured by forming the container, e.g., using a blow-molding, injection molding, or other process, and inserting the insert into the container. For example, the insert may be pressed into position in the container. In some examples, the insert is formed by injection-molding or machining the post, and affixing the porous tip onto the post. For example, the porous tip may be adhered, welded or otherwise disposed on the post. In some instances, the porous tip may comprise one or more porous blanks fixed to the post and/or another porous blank. Once fixed to the post, the porous blanks may be cut or otherwise manipulated to form the desired shape of the porous tip. Alternatively, the porous tip or a blank from which the porous tip may be formed, may be molded onto the post, e.g., using an over-molding process. Once the insert is retained in the container, a cap (e.g., the cap 106) may be molded onto the applicator.

Although embodiments have been described in language specific to structural features and/or methodological acts, it is to be understood that the invention is not necessarily limited to the specific features or acts of the embodiments described. Rather, the specific features and acts are disclosed as illustrative forms of implementing the invention. For example, while embodiments are described having certain shapes, sizes, and configurations, these shapes, sizes, and configurations are merely illustrative. Also, while some example manufacturing processes are described, applicators according to this disclosure may be made using any other suitable manufacturing process.

The invention claimed is:

1. An applicator comprising:
   a container defining a reservoir adapted to contain a substance and including a neck defining an opening;
   an elongate insert comprising an axial post and a flange extending radially outwardly from the axial post, the insert being at least partially disposed in the container such that the flange is at least partially disposed in the neck;
   one or more passageways disposed in the insert fluidly connecting a first side of the flange proximate the reservoir with a second side of the flange, spaced from the first side of the flange along the axial direction;
   a porous tip fixed on the elongate insert covering the one or more axial passageways; and
   a removable cover covering the porous tip.

2. The applicator of claim 1, wherein the one or more passageways comprise openings extending through the flange from the first side of the flange to the second side of the flange.

3. The applicator or claim 1, wherein the one or more passageways comprise one or more axially-extending grooves formed in an outer surface of the flange.

4. The applicator of claim 3, wherein a portion of the porous tip is disposed between the outer surface of the flange and an inner surface of the neck.

5. The applicator of claim 4, wherein an outer surface of the porous tip forms an interference fit with the inner surface of the neck.

6. The applicator of claim 1, wherein the container is deformable, and deformation of the container causes the volume of the reservoir to decrease, forcing the substance in the reservoir to leave the reservoir through the one or more passageways.

7. The applicator of claim 1, further comprising a lip extending radially inwardly from a distal end of the neck and contacting a side of the porous tip.

8. The applicator of claim 1, wherein the removable cap is secured to the container.

9. The applicator of claim 1, further comprising a barb disposed on the axial post a distance from the first side of the flange and extending radially outwardly from the axial post, the barb being disposed in the container.

10. The applicator of claim 9, wherein the barb is deformable between a first position in which a portion of the barb is relatively closer to the post to allow the elongate insert to be inserted into the container and a second position in which the portion of the barb is relatively farther from the post to retain the elongate insert in the container.

11. An applicator comprising:
    a container comprising:
    a deformable base defining a reservoir configured to contain a substance to be dispensed from the container,
    a neck defining an opening of the base, and
    a cover removable from the base to expose the opening; and
    a swab disposed in the container, the swab comprising:
    a post extending generally along an axis of the container,
    a flange extending radially outwardly from the post,
    one or more passageways fluidly connecting a first side of the flange adjacent the reservoir to a second side of the flange opposite the first side, and
    a porous tip covering the flange.

12. The applicator of claim 11, wherein the one or more passageways comprise one or more grooves formed in an outer surface of the flange and extending from the first side of the flange to the second side of the flange.

13. The applicator of claim 11, wherein the porous tip comprises an open cell foam.

14. The applicator of claim 11, wherein the swab is disposed in the container such that the flange is at least partially in the neck of the container.

15. The applicator of claim 11, wherein the one or more passageways comprise a passageway extending at least partially through the axial post.

16. An applicator comprising:
    a deformable container defining a reservoir adapted to contain a substance and terminating at a neck defining an opening;

an insert comprising a post extending from a proximal end to a distal end and a flange between the proximal end and the distal end extending radially outwardly from the post, the insert being at least partially disposed in the container such that the flange is at least partially disposed in the neck;

one or more grooves formed on an outer surface of the flange and extending from a first side of the flange proximate the reservoir to a second side of the flange, spaced from the first side of the flange in an axial direction;

a porous tip fixed on the elongate insert covering the one or more axial passageways, an outer surface of the porous tip forming an interference fit with the neck of the deformable container; and a removable cap covering the porous tip.

17. The applicator of claim 16, wherein the proximal end of the post is disposed in the reservoir and the porous tip covers the distal end of the post.

18. The applicator of claim 16, wherein the removable cap is fixed to a distal end of the neck at a frangible connection.

19. The applicator of claim 18, wherein the frangible connection is broken in the presence of a shear force created by rotating the removable cap relative to the container.

20. The applicator of claim 19 further comprising a grip disposed on the removable cap.

* * * * *